United States Patent [19]

Yabuki et al.

[11] Patent Number: 5,066,590

[45] Date of Patent: Nov. 19, 1991

[54] SUPEROXIDE DISMUTASE COMBINED WITH A POLY(ALKYLENE OXIDE)

[75] Inventors: Akira Yabuki; Yuji Iwashita, both of Kawasaki, Japan

[73] Assignee: Ajinomoto Co., Inc., Tokyo, Japan

[21] Appl. No.: 304,914

[22] Filed: Feb. 2, 1989

Related U.S. Application Data

[63] Continuation of Ser. No. 854,792, Apr. 23, 1986, abandoned.

[30] Foreign Application Priority Data

Apr. 26, 1985 [JP] Japan .................................. 60-90605

[51] Int. Cl.$^5$ ...................... C12N 11/08; C12N 9/02; A61K 37/50
[52] U.S. Cl. .................................... 435/180; 435/175; 435/177; 435/188; 435/189; 424/94.3; 424/94.4
[58] Field of Search ............................ 424/94.3, 94.4; 435/188, 189, 175, 177, 180

[56] References Cited

U.S. PATENT DOCUMENTS 3,654,083  4/1972  Moelker ................................. 195/63

FOREIGN PATENT DOCUMENTS 0070656  1/1983  European Pat. Off. .

OTHER PUBLICATIONS

Boccu, E. et al. (1983), Zeitschrift Fuer NaturForschung 38, 94–99.

F. M. Veronese et al., "Anti-Inflammatory and Pharmacokinetic Properties of Superoxide Dismutase Derivatized with Polyethylene Glycol via Active Esters", Chemical Abstracts, vol. 100, No. 3, Jan. 16, 1984, pp. 28–29.

C. O. Beauchamp et al., "A New Procedure for the Synthesis of Polyethylene Glycol-Protein Adducts; Effects on Function, Receptor Recognition, and Clearance of Superoxide Dismutase, Lactoferrin, and Alpha2-Macroglobulin", Chemical Abstracts, vol. 99, No. 5, Aug. 1, 1983, p. 284.

*Primary Examiner*—Jacqueline Stone
*Attorney, Agent, or Firm*—Oblon, Spivak, McClelland, Maier & Neustadt

[57] ABSTRACT

Superoxide dismutase is chemically modified with poly(alkylene oxide), the modified superoxide dismutase having a molecular structure in which both ends of a poly(alkylene oxide) molecule are attached to superoxide dismutase. The modified superoxide dismutase can be used to remove toxic substances derived from oxygen, from the blood circulation in a living body, and has a longer half life in the blood circulation as compared to superoxide dismutase which has not been modified.

11 Claims, 4 Drawing Sheets

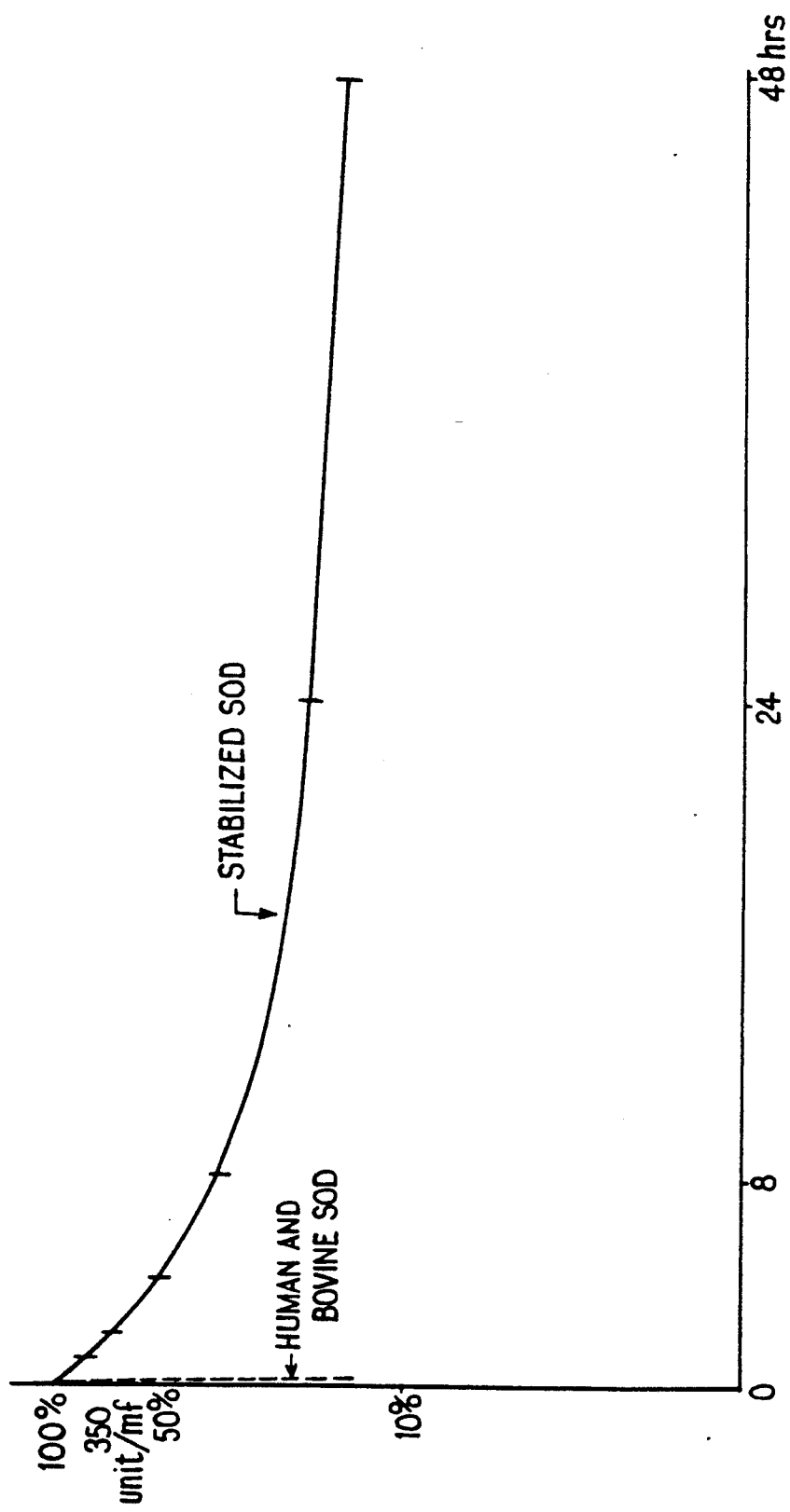

SUPEROXIDE DISMUTASE COMBINED WITH A POLY(ALKYLENE OXIDE)

This application is a Continuation of application Ser. No. 06/854,792, filed on Apr. 23, 1986, now abandoned.

BACKGROUND OF THE INVENTION

1. Field of the Invention

The present invention relates to a novel stabilized superoxide dismutase, hereinafter referred to as "stabilized SOD" or "modified SOD", for use as an active ingredient of medicines such as anti-inflammatory agents, ischemic disease treating agents, cardiac infarction treating agents, radial ray lesion treating agents, tumor metastasis-preventing agents and stroke treating agents.

2. Description of the Prior Art

Superoxide dismutase, hereinafter referred to as "SOD", can be employed as the medicines mentioned above, since it can remove toxic substances derived from oxygen, in a living body.

However, when SOD is administered in the living body by intravenous injection, the half life of the SOD in the blood circulation is only a few minutes. Therefore the administered SOD is rapidly lost from the circulation in the living body. Accordingly, the enzymatic activity of the SOD cannot be retained for a time sufficient to remove toxic substances to a sufficient extent. Moreover, it causes adverse reactions by the over administration of SOD to the living body.

In order to resolve the problems mentioned above, many chemical modifications of SOD have been performed in order to extend the life of SOD in the circulation of the living body. The half life time (T-50) of chemically modified SOD in the circulation varies dependent upon the molecular weight of the modified SOD, and therefore modified SOD having a high molecular weight is expected to have a greater half survival time (see (1) E. Boccu, G. P. Velo, F. M. Veronese, Pharmacol., Res. Commun., 14, 113, 1982; (2) E. Boccu, R. Largajolli, F. M. Veronese, Z. Naturforschung, 38, 94, 1983; and (3) Pyatak et al, Res. Commun. Chem. Pathol. Pharm. 29, 113, 1980).

In these cases, a large number of poly(alkylene oxide) molecules of which one terminal group is protected with a methoxy group, are chemically attached to one SOD molecule through the other terminal group of the poly(alkylene oxide) to obtain a high molecule weight SOD derivative).

The method used for the modification of SOD with Ficoll, rat albumin and with poly(ethylene oxide) by P. S. Pyatak et al, is not good enough to be employed for medical uses because the SOD activity is as low as 50% of the original enzyme.

On the other hand, in the method for modification with methoxypolyethylene glycol as described by Boccu et al (see references (1) and (2) above), it is not possible to obtain a product having an enzyme activity sufficiently high for medical purposes and having a long half survival time in the blood circulation.

SUMMARY OF THE INVENTION

The inventors of the present invention have attempted to solve the above problems and to develop modified SOD whose SOD activity is high and whose half survival time in the blood circulation is long, and have succeeded in the production of a novel superoxide dismutase combined chemically with a poly(alkylene oxide), wherein said modified superoxide dismutase has a molecular structure in which both ends of a poly(alkylene oxide) moiety are attached to superoxide dismutase, and have found that this modified superoxide dismutase is very stable in the blood circulation and moreover, that the SOD activity is not lost by the chemical modification. They have thus solved the above problems. Thus, the present invention provides, in a superoxide dismutase chemically modified with poly(alkylene oxide), the improvement wherein said modified superoxide dismutase has a molecular structure in which both ends of a poly(alkylene oxide) molecule are attached to superoxide dismutase. In a modification, only one end of said poly(alkylene oxide) is attached to superoxide dismutase, the other end thereof comprising a carboxyl group protected by an amino acid (e.g. glycine or lysine). The present invention also provides a pharmaceutical composition comprising modified superoxide dismutase of the invention, and a pharmaceutically-acceptable carrier or diluent.

BRIEF DESCRIPTION OF THE DRAWINGS

Reference will be made hereinafter, by way of example, to the drawings in which:

FIG. 5 is a graph showing the activity changes of the stabilized SOD obtained by Example 1 hereinbelow, and of human and bovine SOD, in the blood circulation.

DESCRIPTION OF THE PREFERRED EMBODIMENTS

The stabilized SOD of the present invention preferably has a number average molecular weight of from 70,000 to 500,000, more preferably from 70,000 to 200,000. Furthermore, it usually has a high SOD activity of from 85 to 100%.

The number of said poly(alkylene oxide) molecules attached to one molecule of SOD is usually from 0.5 to 10, preferably from 1 to 6.

The poly(alkylene oxide) used in the present invention is preferably a polymer soluble in water, for example, poly(ethylene oxide), poly(propylene oxide), or a copolymer of ethylene oxide and propylene oxide. The molecular weight of the polymer is preferably about 400 to 20,000.

In the reaction for the production of the stabilized SOD, poly(alkylene oxide) having carboxyl groups at both ends of the molecule is preferably used as a starting material. The structure of the end of the molecule is, for example, one of the following structures:

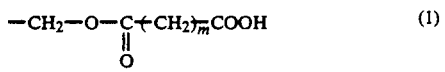  (1)

  (2)

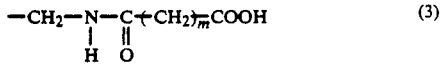  (3)

wherein m is an integer of from 1 to 12.

Having regard to the stability of the product, the above structures (2) and (3) are preferred.

The poly(alkylene oxide) derivative having carboxyl groups at both ends of the molecule can be produced, for example, by the following methods.

In case of the structure (2) mentioned above, the poly(alkylene oxide) can be oxidized with oxygen in the presence of an oxidizing catalyst such as platinum or palladium. Hydroxyl groups at both ends of the poly(alkylene oxide) may be reacted with an acid such as a monohalogenated carboxylic acid, a diazo carboxylic acid or the like.

In case of the structure (3) mentioned above, the hydroxyl groups at both ends of the poly(alkylene oxide) may be reacted with tosyl chloride and hydrazine to form an amino group (see M. Mutter, Tetrahedron Letters 2839, 1978), and then the thus formed amino group may be reacted with a dicarboxylic acid to form an amide bond.

The stabilized SOD of the present invention can contain any SOD modified chemically with poly(alkylene oxide), provided that said modified SOD has a structure in which both end groups of a poly(alkylene oxide) molecule are attached to the SOD. Examples thereof are shown in FIG. 1, in which the divided circles indicate SOD molecules and the meandering lines indicate poly(alkylene oxide) moieties.

The stabilized SOD of the present invention can be obtained by combining the poly(alkylene oxide) (or an activated derivative thereof as mentioned above as obtained above, with SOD via an amide bond.

Figure 1:
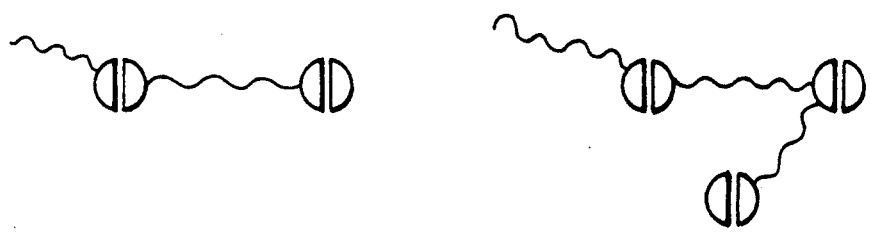
FIG. 1 illustrates SOD molecules in accordance with the invention.
Figure 1:
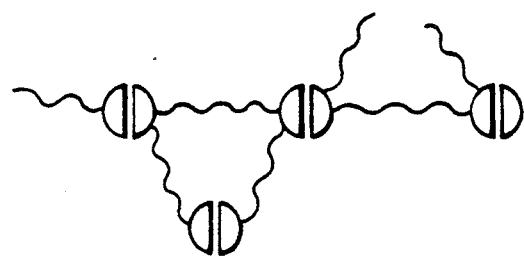

In the stabilized SOD of the present invention, there can be present not only one molecule as shown in FIG. 1, but also a mixture containing at least some or all of the molecules.

The amide bond is preferably formed by the use of a coupling agent such as 1-ethyl-3-(3-dimethylaminopropyl)-carbodiimide hydrochloride. Another preferred method involves the use of a carboxylic acid-activating agent, as in ordinary peptide synthesis, such as N-hydroxy succinimide, N-hydroxy phthalimide, p-nitrophenol, or pentachlorophenol, with the help of dicyclohexylcarbodiimide, to produce an activated ester of the poly(alkylene oxide) and the reaction of the activated ester with SOD to exchange an amide group. The latter method, using the active ester, is better than the former from the viewpoint of obtaining a modified enzyme of high activity.

The reaction of the SOD is preferably carried out as follows. SOD is dissolved in water or in a buffer of pH 6.5 to 10.0, preferably from 7.2 to 8.5, wherein the concentration of SOD is from 0.1 to 10%, preferably from 0.5 to 3%, and then the activated poly(alkylene oxide) is added thereto in an amount of from 1 to 100 moles, preferably from 2 to 15 moles, of the activated poly(alkylene oxide) derivative to one mole of SOD. By adjusting the concentration of SOD, and the molar amount of the activated poly(alkylene oxide) added, the molecular weight of the stabilized SOD can be controlled.

If the reaction between the poly(alkylene oxide) and the SOD is carried out in the presence of an amino acid such as glycine or lysine, and an amine such as monoethanol amine, it is easier to obtain stabilized SOD of a preferred molecular weight distribution, the preferred molecular weight being 70,000 to 200,000. In particular, when the concentration of the SOD is over 2.5%, the addition of the amino acid is useful to control the molecular weight so as to fall in the desirable range as given above.

As mentioned before, the SOD of the present invention may be not only a single compound, for example, as illustrated in FIG. 1, but also a composition containing at least one of these single compounds. Also, a composition having a desired ratio of single compounds, one to another, can be easily produced.

The SOD of this invention is not limited to the kinds of molecules illustrated in FIG. 1, but includes molecules of modified SOD of a higher molecular weight than those shown in FIG. 1, and also includes modified SOD having various structural formulae.

The stabilized SOD as produced is usually in the form of a mixture of molecules, rather than in the form of a single molecule, and of course all of these molecules are within the scope of the present invention. Moreover, the stabilized SOD may contain impurities such as the starting material or non-crosslinked compounds which do not contain a crosslinked structure. Such a composition is within the scope of the present invention, particularly when the physicochemical properties, such as the range of molecular weight, are given above.

The SOD used as a starting material in the present invention includes that obtained from mammals such as cattle, swine, sheep and horses, that obtained from microorganisms such as *Escherichia Coli*, that obtained from microorganisms obtained by means of genetic engineering, that produced by yeasts, and the like. The source of the SOD is not limited.

EXAMPLES

The present invention will now be illustrated by the following Examples.

Example 1

An aqueous solution (500 ml) of platinum-palladium-carbon (20 g) as a catalyst, produced by the method disclosed in JP-A-141219/1978 (Kawaken Fine Chemical Co., Inc.), and a poly(ethylene oxide) (200 g) made by Nihon Yushi Co., Inc., Japan (namely Macrogol 4000) were placed in an autoclave and pressured air was fed into the autoclave to adjust the pressure to 10 kg/cm$^2$. The mixture was reacted for 10 hours at 90° C.

The catalyst was removed by filtration from the reaction mixture. The solution thus obtained was treated with activated carbon and then recrystallized from water to obtain an acid derivative of poly(ethylene oxide) having carboxyl groups at both ends thereof, in a yield of 180 g.

The thus-obtained α-carboxymethyl, ω-carboxymethoxy polyoxyethylene (molecular weight: about 4000) (4.0 g, 0.001 mole) and N-hydroxysuccinimide (0.46 g, 0.004 mole) were dissolved in N,N-dimethylformamide (DMF) (300 ml), and then dicyclohexylcarbodiimide (DCC) (0.84 g, 0.004 mole) was added thereto. The mixture was stirred at room temperature overnight.

The crystals of dicyclohexyl urea that formed were separated by filtration. To the filtrate, ethyl ether (600 ml) was added to precipitate crystals of succinimidyl derivative. The crystals were separated by filtration, washed well with ethyl ether, and dried to give white crystals of the polyoxyethylene derivative of the activated ester (4.2 g).

Superoxide dismutase (SOD) (3000 units/mg; 100 mg, 0.003 mmole) derived from a bovine blood produced by Toyobo Co., Japan was dissolved in 0.1M phosphate buffer (4 ml) adjusted to pH 7.4, and then the activated derivative as obtained above (37 mg, 0.009 mmole) was added thereto. Thereafter, the mixture was stirred for 3 hours at ice temperature.

The molecular weight of the stabilized SOD changed during the first one hour from the start of the reaction. After three hours from the start, the reaction was almost completed. After the completion of the reaction, the activity of the SOD was determined, and the residual activity was found to be 95±5% (total activity: 285000 units) in comparison with the original SOD.

The reaction mixture was filtered repeatedly using an ultra filtration membrane capable of hindering the passage of molecules of molecular weight over 30,000, to remove unreacted active ester and the decomposed substances therefrom, and to obtain a modified SOD solution. The product was freeze-dried to obtain stabilized SOD in a yield of 107 mg.

The yield of protein of the stabilized SOD was 83%, the total activity thereof was 236000 units (the residual activity being 95%), and the average number of poly(ethylene oxide) molecules attached to one mole of the enzyme was 2.4.

Example 2

SOD derived from human erythrocyte purchased from Sigma Co. (2300 units/mg) was filtered by gel filtration using "Sephadax G-100 Super fine" produced by Pharmacia Co., Sweden. Fractions having a molecular weight of 32000 and of approximately 32000 were collected and the thus purified human SOD (3050 units/mg) (50 mg, 0.0015 mmole) was dissolved in 0.1M phosphate buffer (pH 7.4; 2.5 ml), and then the activated poly(ethylene oxide) derivative obtained in Example 1 (30 mg, 0.0075 mmole) was added thereto. The mixture was stirred for 3 hours in an ice bath, and then was filtered repeatedly by ultrafiltration to obtain a fraction with a molecular weight of 30,000. The product was freeze-dried to obtain stabilized SOD in a yield of 60 mg.

The yield of protein of the stabilized SOD was 85%, the residual activity thereof was 94±5%, and the average number of poly(ethylene oxide) molecules attached to one mole of the SOD enzyme was 3.5.

Example 3

Commercially available "Pluronic P-94" produced by BASF Wyandotte Co., USA (a block copolymer of ethylene oxide and propylene oxide, average molecular weight: 2750) (11.2 g, 4 mmole) and γ-bromo-n-butyric acid ethyl ester (7.8 g, mmole) were dissolved in well-dehydrated DMF (300 ml), and silver oxide (15 g) was added thereto. The mixture was stirred for 24 hours at 50° to 60° C. The reaction mixture was subjected to filtration to remove solid substances.

The thus obtained filtrate was added to ethyl ether (2.0 liters) to precipitate the required product. The precipitated substance was further washed well with ethyl ether, dried and dissolved again in water (200 ml). The aqueous solution was warmed to 40° to 50° C., and then 2N aqueous sodium hydroxide solution was slowly added dropwise thereto under stirring to adjust the pH value thereof to a value of 11 to 12.

After adjustment of pH, the mixture was stirred continuously for 2 hours, and 1N aqueous hydrochloric acid solution was added thereto to adjust the pH to 6. Water was removed from the reaction mixture by a rotary evaporator. The thus obtained solid substance was dissolved again in DMF (100 ml). Insoluble material was removed by filtration, and the filtrate was added to ethyl ether (1 liter) to precipitate crystals. The crystals were recovered by filtration, washed well with ethyl ether and dried to obtain white crystals in a yield of 10.5 g.

The white crystals were dissolved in 0.05M phosphate buffer (pH 7.4) (200 ml), and the solution was loaded onto a column of the anion exchange resin ("BIO-RAD 1×2" produced by BIORAD Co,; resin content: 300 ml) equilibrated with the same buffer solution, so that a Pluronic derivative having a terminal carboxyl group was adsorbed onto the resin. The adsorbed Pluronic derivative was eluted with 0.05M aqueous hydrochloric acid solution. The eluate was freeze-dried to obtain white crysals in a yield of 7.2 g.

Thereafter, in the same manner as in Example 1, the Pluronic derivative activated ester was obtained.

Bovine SOD (50 mg, 0.0015 mmole, 3000 units/mg) produced by Toyobo Co., Japan, was dissolved in 0.1M phosphate buffer (pH 7.4, 5 ml), and then the above activated ester (33.5 mg, 0.0105 mmole) was added to the mixture, in an ice bath. The mixture was reacted for 3 hours to obtain stabilized SOD (55 mg).

The average number of copolymer molecules attached to one mole of the SOD was 5.3, and the residual activity thereof was 85%.

Example 4

Both ends of poly(ethylene oxide) having an average molecular weight of 1000 daltons were oxidized in the same manner as described in Example 1. The thus obtained poly(ethylene oxide) derivative (4.0 g, 4 mmole) and para-nitrophenol (1.66 g, 12 mmole) were dissolved in DMF (150 ml), and dicyclohexyl carbodiimide (2.48 g, 12 mmole) was added thereto. The mixture was reacted at room temperature overnight.

After the completion of the reaction, dicyclohexyl urea was removed by filtration, and to the filtrate ethyl ether (2 liters) was added to precipitate crystals. The crystals were washed well with ethyl ether and dried to obtain white crystals in a yield of 3.8 g.

Bovine SOD (60 mg), produced by Toyobo Co. (3000 units/mg, 0.0018 mmole) and glycine (1.1 mg, 0.015 mmole) were dissolved in 0.1M phosphate buffer (pH 8.2, 2 ml), and then the poly(ethylene oxide) derivative activated ester as obtained above (17 mg, 0.014 mmole) was added thereto. The mixture was reacted for 3 hours in an ice bath to obtain stabilized SOD in a yield of 62 mg.

The average number of poly(ethylene oxide) molecules attached to one mole of the SOD was 4.5, and the residual activity thereof was 90±5%.

Example 5

Poly(ethylene oxide) having an average molecular weight of 3800 daltons was reacted by the method of M. Mutter (Tetrahedron Letters, 2839, 1978) to form a derivative thereof having amino groups at both ends, the structure of both ends being —O—CH$_2$—CH$_2$—NH$_2$. The thus obtained derivative (5 g, 1.3 mmole) was dissolved in well-dehydrated dioxane (100 ml), and succinic anhydride (2.5 g, 25.0 mmole) was added thereto. The mixture was reacted for 20 hours at room temperature. The reaction solution was added to ethyl ether (1 liter) to obtain a poly(ethylene oxide) derivative having carboxyl groups at both ends thereof in a yield of 4.8 g.

The thus obtained poly(ethylene oxide) derivative was activated by method described in Example 1, to produce the activated derivative therof.

Bovine SOD (50 mg, 0.0015 mmole, 3000 units/mg), produced by Toyobo Co., Japan was dissolved in 0.1M phosphate buffer (pH 7.5, 2.5 ml), and then the activated poly(ethylene oxide) derivative as mentioned above (28 mg, 0.009 mmole) was added thereto. The mixture was stirred for 3 hours in an ice bath to obtain stabilized SOD.

The average number of poly(ethylene oxide) molecules attached to one mole of the SOD was 4.2, and the residual activity thereof was 88%.

Example 6 (Prevention of tumor metastasis)

$10^6$ cells of Lewis-lung tumor were implanted onto the foot of a number of C57BL-6 mice, and the implanted tumor was removed at seventh day after the transplantation (n=7).

The modified SOD (m-SOD) obtained in Example 1 was dissolved in a saline solution (5 mg by SOD content in 1 ml saline solution). To the mice, the modified SOD solution (2 mg by SOD content per kg) was injected intravenously once a day for 5 days from the seventh day or fourteenth day after the transplantation.

On the 22nd day after the transplantation, the lungs were taken out and the number of colonies of metastasizing cells was determined. The inhibition of the metastasis was evaluated by the decrease of the number of colonies and the weight of metastasizing lung tumor. The results are given in Table 3 below.

The number of colonies and the weight of tumor in the mice treated with the modified SOD decreased below 40% as compared to the non-treated mice.

The average number of poly(alkylene oxide) molecules attached to the one mol of the modified SOD as produced by the above Examples was determined by the following method.

The weight of the modified SOD as obtained by freeze-drying was measured, and the sample was dissolved in water so as to give a solution having a concentration of a few percent. The absorption at 650 to 700 nm thereof (Bovine SOD: 680 nm, Human SOD: 655 nm) were obtained and thereby the amount of SOD as the starting material was determined (Bovine SOD: E=300; Human SOD: E=350). The ratio by weight of the modified product to the non-modified product was calculated, and thereby the amount of poly(alkylene oxide) attached to the SOD was determined.

The residual activity was obtained by the following method. The starting SOD material and the modified SOD as obtained above were dissolved in appropriate volumes of a buffer solution, and the enzyme activity was determined by the method of J. M. McCord et al (J. Biol. Chem., 244, 6049, 1969).

The concentration of each enzyme was obtained by the absorption method as mentioned above, and the residual activity was calculated from a comparison in activity after the reaction.

The residual activity and number average molecular weight of each stabilized SOD as obtained in the Examples is given in Table 1 below.

Figure 2:
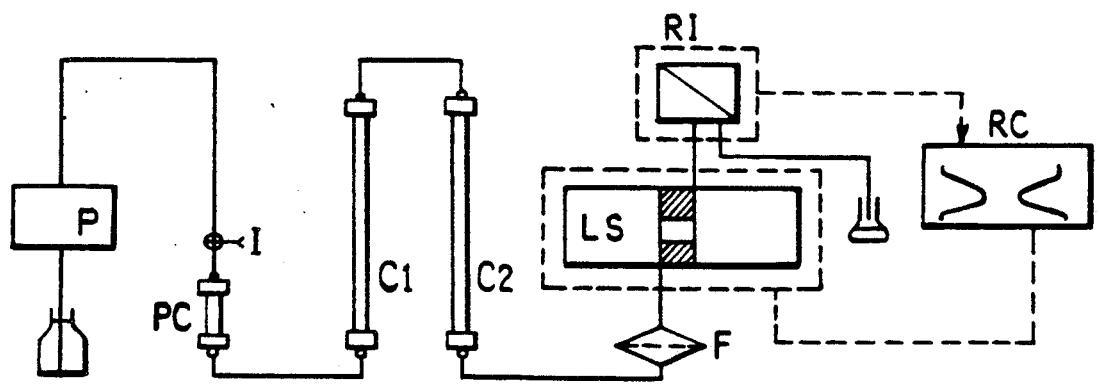
FIG. 2 illustrates an apparatus for the measurement of the molecular weight of SOD molecules.

The number average molecular weight was determined by a small angle laser light scattering method, using an apparatus as shown in FIG. 2. As shown in FIG. 2, this apparatus consists of a pump P (namely an HPLC pump made by Nihon Bunko Co., TRIROTAR VI type), an injector I, a pre-column PC (Guard Column-SW, Toyo Soda Co.), a first separation column $C_1$ (G4000SW, 7.5 mm in diameter and 60 cm in length, Toyo Soda Co.), a second separation column $C_2$ (G3000SW, 7.5 mm in diameter and 60 cm in length, Toyo Soda Co.), a filter F (produced by TEFURON), a small angle laser light scattering apparatus LS (Toyo Soda Co., LS-8), a refractometer RI (Toyo Soda Co., RI-8011), and a recorder RC (in which the eluent was 0.1M phosphate buffer (pH 6.8) plus 5% ethanol, and the flow rate was 0.5 ml/minute).

As shown in the Figure, the fractionation for the determination of molecular weight was carried out by the use of prepacked gel permeation columns of "G4000SW and G3000SW" type, as produced by Toyo Soda Co., Inc., Japan. The intensity of scattering and the refractive index (the differential refractive index) were measured by the use of the laser light scattering apparatus LS and the refractometer RI, simultaneously.

The number average molecular weight can be obtained from the following equation:

$M_W = 1/B \cdot S_{LS}/S_{RI}$   $B = k_2 K/k_1$ (a constant)

$S_{LS}$: Intensity of Scattering $S_{RI}$: Change of Refractive Index.

The constant, B, is dependent on the apparatus and the substances to be tested, and bovine serum albumin, the molecular weight of which is known (=67000), is employed for the calculation of $B_o$ as a standard value. For each sample to be tested, the following amended equation is obtained:

$B = B_o [(\Delta n/C)/\Delta n_o/C_o)]$ $B_o$: the value of B obtained in the case of bovine serum albumin;

$\Delta n$: Intensity of Refractive Index of the sample to be tested;

$\Delta n_o$: Intensity of Refractive Index of bovine serum albumin;

C: the concentration of the sample to be tested;

$C_o$: the concentration of bovine serum albumin.

Figure 3:
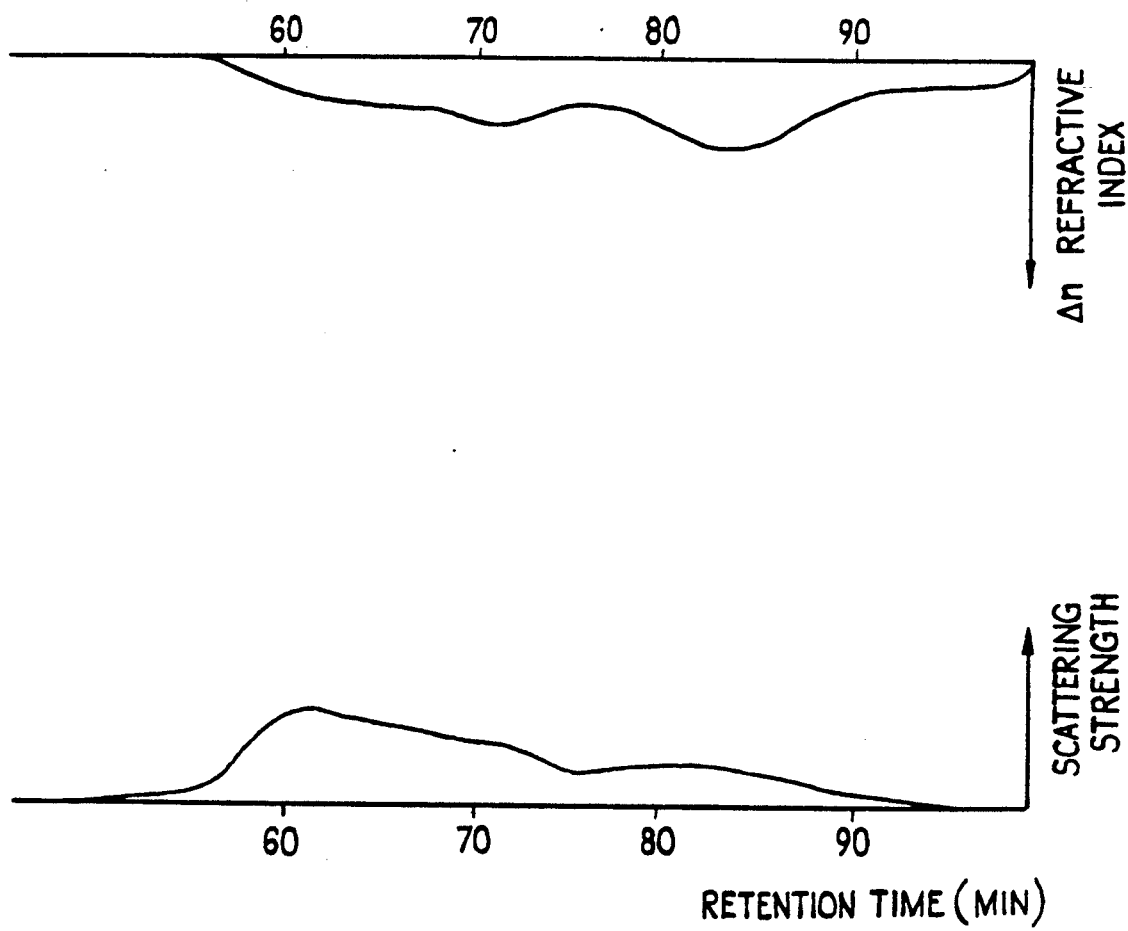
FIGS. 3 and 4 are graphs showing properties of the stabilized SOD obtained by Examples 1 and 4 hereinbelow, respectively.
Figure 4:
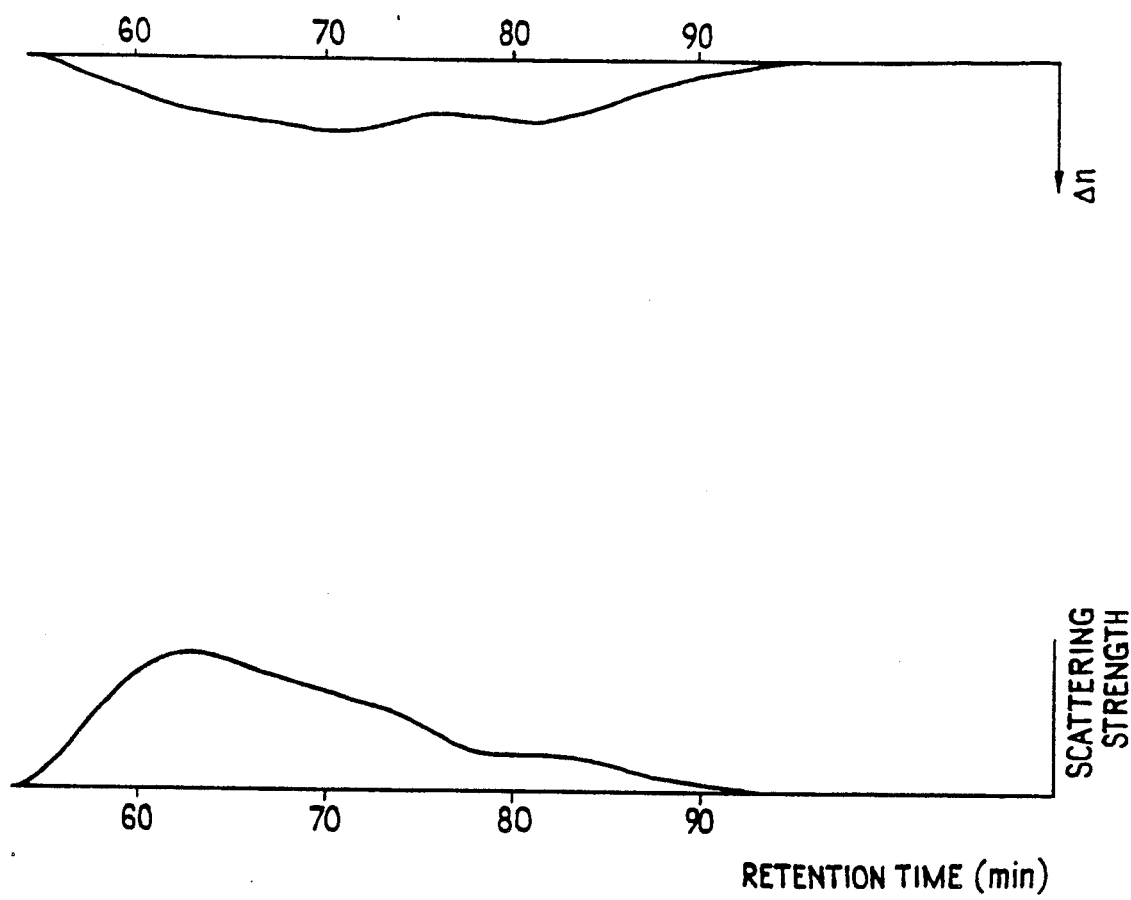

Typical variations are as shown in FIGS. 3 and 4.

For each stabilized SOD obtained in the Examples, the survival time in the blood circulation was measured as follows. Four Wister rats, seven weeks old and weighing 249 to 277 g, were used for each sample. The rats were infused with 20 mg of the sample (20 mg SOD content for the modified SOD; 5 mg per rat) dissolved in a saline solution (0.5 ml per rat) per kg of body weight through the femoral vein, and samples of blood, each 0.2 ml, were withdrawn 5, 15 and 30 minutes and 1, 2, 4, 8, 24 and 48 hours after the injection. Each blood sample was centrifuged, and the SOD activity of the plasma was determined by the method of J. M. McCord et al (J. Biol. Chem.,.244, No. 22, 6049–55, 1969).

The variation with time of the activity in the blood circulation of the stabilized SOD obtained in Example 1 and of bovine and human SOD are as shown in FIG. 5.

As can be seen from the FIG. 5, the activity of the stabilized SOD rapidly reduces after a few hours from the adminstration, and then it reduces slowly.

The half survival time of SOD activity in the circulation for the stabilized SOD obtained by each of the Examples, of human SOD, and of bovine SOD, and the time for the SOD activity of the enzyme derivatives to be lowered to 30% in the blood circulation, are as given in Table 2 below.

From these results, it can be seen that the life of each stabilized SOD in the circulation was very much longer than that of the original SOD.

It was confirmed that the properties, of the stabilized SOD, necessary for use as a medicine, such as pharmacological action and durability thereof, were improved remarkably, and that the stabilized SOD can give a sufficient effect by intravenous injection.

TABLE 1

| Example No. | Number average molecular weight ($\times 10^4$) | Residual enzyme activity (%) |
|---|---|---|
| Example 1 | (number average molecular weight) 7.2 | 95 |
| Example 2 | (number average molecular weight) 8.5 | 94 |
| Example 3 | (number average molecular weight) 12.0 | 85 |
| Example 4 | (number average molecular weight) 15.6 | 90 |
| Example 5 | (number average molecular weight) 10.2 | 88 |
| Monomethoxy-polyethylene glycol conjugated SOD | | |
| (reference 3) | 13 | 51 |
| (reference 1) | 3.7 | 70–90 |
| (reference 1) | 12.1 | 50 |
| (reference 2) | 4.6 | 90 |
| (reference 2) | 12.1 | 70 |

TABLE 2

| Sample | Half life (hrs) | Time to 30% residual activity (hrs) |
|---|---|---|
| Example 1 | 4 | 10 |
| Example 2 | 5 | 14 |
| Example 3 | 6 | 20 |
| Example 4 | 8 | 30 |
| Example 5 | 6 | 15 |
| bovine SOD (control) | 0.1 | 0.15 |
| Human SOD (control) | 0.1 | 0.15 |

TABLE 3

| | Mean number of tumor colonies | Inhibition ratio (%) | Mean weight of lung tumor (g) | Inhibition ratio (%) |
|---|---|---|---|---|
| Control (5 injections of saline) | 30.3 | — | 0.44 | — |
| m-SOD (5 injections after 7th day) | 10.5 | 65 | 0.15 | 66 |
| m-SOD (5 injections after 14th day) | 8.4 | 72 | 0.10 | 77 |

We claim:

1. A modified superoxide dismutase having a molecular structure in which both ends of a poly(alkylene oxide) molecule are attached to superoxide dismutase.

2. A modified superoxide dismutase as set forth in claim 1, wherein said poly(alkylene oxide) is selected from the group consisting of poly(ethylene oxide), poly(propylene oxide), and copolymers of ethylene oxide and propylene oxide.

3. A modified superoxide dismutase as set forth in claim 1, wherein each of said ends of said poly(alkylene oxide) comprises a carbonyl group.

4. A modified superoxide dismutase as set forth in claim 3, wherein each of said ends of said poly(alkylene oxide) has the structure: $-CH_2-O-(CH_2)_m-CO$ wherein m is an integer of 1 to 12.

5. A modified superoxide dismutase as set forth in claim 3, wherein each of said ends of said poly(alkylene oxide) has the structure: $CH_2-NH-CO-(CH_2)_m-CO-$ wherein m is an integer of 1 to 12.

6. A modified superoxide dismutase as set forth in claim 1, wherein the average number of said poly(alkylene oxide) molecules attached to one molecule of superoxide dismutase is from 0.5 to 10.

7. A modified superoxide dismutase as set forth in claim 1, wherein said poly(alkylene oxide) has a molecular weight of from 400 to 20,000.

8. A modified superoxide dismutase as set forth in claim 1, having a number average molecular weight of from 70,000 to 500,000.

9. A pharmaceutical composition comprising modified superoxide dismutase as set forth in claim 1, and a pharmaceutically-acceptable carrier or diluent.

10. A modified superoxide dismutase having a number average molecular weight of over 70,000 daltons and having a molecular structure in which both ends of a poly(alkylene oxide) molecule are attached to superoxide dismutase.

11. The modified superoxide dismutase of claim 10, prepared by reacting, at a pH of 7.0 to 11.0, superoxide dismutase in a concentration of 0.5 to 5.0% by weight with a 5 to 100 molar excess amount of poly(alkylene oxide), based on the quantity of said dismutase.

* * * * *